United States Patent [19]

Birum et al.

[11] Patent Number: 4,739,116
[45] Date of Patent: * Apr. 19, 1988

[54] PREPARATION OF ARYLSULFONAMIDES

[75] Inventors: Gail H. Birum, Kirkwood; Richard F. Jansen, St. Louis, both of Mo.

[73] Assignee: Akzo America Inc, New York, N.Y.

[ * ] Notice: The portion of the term of this patent subsequent to Dec. 15, 2004 has been disclaimed.

[21] Appl. No.: 820,875

[22] Filed: Jan. 16, 1986

Related U.S. Application Data

[63] Continuation of Ser. No. 662,731, Oct. 19, 1984, abandoned.

[51] Int. Cl.⁴ .......................................... C07C 143/38
[52] U.S. Cl. ...................................................... 564/90
[58] Field of Search ........................................ 564/90

[56] References Cited

U.S. PATENT DOCUMENTS

| | | | |
|---|---|---|---|
| 2,182,262 | 5/1935 | Mitchell | 106/40 |
| 2,658,916 | 11/1953 | Krems | 564/90 |
| 2,757,156 | 7/1956 | Dazzi | 260/30.8 |
| 3,246,007 | 4/1966 | Meyer et al. | 260/307 |
| 4,378,444 | 3/1983 | Barenberg et al. | 564/169 |

OTHER PUBLICATIONS

*The Merck Index*—10th Edition, Martha Windholz—Editor, Merck and Co., Inc., Rahway, N.J., 1983, p. ONR-82.

*Organic Chemistry of Sulfur*, C. M. Suter, John Wiley and Sons, Inc., (1944), pp. 573–578.

*Primary Examiner*—Anton H. Sutto
*Attorney, Agent, or Firm*—Francis W. Young; Louis A. Morris

[57] ABSTRACT

A process improvement for the preparation of arylsulfonamides that avoids the multistep arylsulfonyl chloride refining operation presently used and, in one step, neutralizes and removes all the acidic by-products of chlorosulfonation simultaneously with arylsulfonamide formation which comprises the steps of (a) reacting an aryl hydrocarbon with chlorosulfonic acid to form a crude chlorosulfonation reaction product, (b) combining in an aqueous media said crude reaction product and a source of ammonia to form an amidation reaction mixture, (c) maintaining the temperature of the amidation reaction mixture at between about 40° C. and 70° C. and the pH at above about 7 with stirring for a period of time sufficient to form an amidation reaction product containing an arylsulfonamide, and optionally (d) separating the resulting arylsulfonamide from the amidation reaction product.

16 Claims, No Drawings

PREPARATION OF ARYLSULFONAMIDES

This is a continuation of application Ser. No. 662,731, filed Oct. 19, 1984, now abandoned.

BACKGROUND OF THE INVENTION

This invention relates to an improved process for the synthesis of arylsulfonamides. More particularly, the invention relates to the preparation of arylsulfonamides by reacting ammonia with the crude reaction product from the reaction of an aryl hydrocarbon and chlorosulfonic acid without separation of by-products or unreacted materials from the aryl sulfonyl chloride present in the crude reaction product.

A typical method for the preparation of arylsulfonamides, as set forth in *The Organic Chemistry of Sulfur*, by C. M. Sutter, John Wiley & Sons, Inc., (1944), pages 573–578, involves the use of an aryl sulfonyl chloride compound, generally prepared from the reaction of chlorosulfonic acid with a suitable aryl compound such as benzene, alkyl substituted benzene compounds, naphthalene and the like. The aryl sulfonyl chloride is then reacted with ammonia. The reaction is usually conducted in an inert solvent such as benzene, employing two equivalents of ammonia for one of the sulfonyl chloride, or in the presence of aqueous alkali where only one equivalent of ammonia may be necessary. Where the starting ingredients are a solid, the addition of an organic solvent immiscible with water is usually desirable. Alternatively, the reaction may also be carried out in the presence of triethyl amine or pyridine.

In order to avoid contamination, maintain sufficient yields and avoid the possibility of undesirable side reactions, the sulfonyl chloride used in preparing sulfonamides is typically refined, usually by water quenching, washing in the presence of a solvent, solvent stripping, distillation, and sometimes crystallization, to remove by-products and unreacted ingredients which may be present from the preparation of the sulfonyl chloride.

U.S. Pat. No. 2,757,156 to Dazzi discloses preparation of N-alkyl alkene sulfonamides by reacting a paraffin with a mixture of sulfur dioxide and chlorine followed by reacting the resulting sulfonyl chloride with a primary alkyl amine. In an example, N-heptane sulfonyl chloride is prepared and then recovered by distillation of the reaction product prior to reaction with monoethylamine.

U.S. Pat. No. 3,246,007 to Meyer et al discloses oxadiazole benzene sulfonamide compounds. In the examples, the intermediate benzene sulfonyl chloride is isolated and purified prior to reaction with the amines.

Such refined aryl sulfonyl chloride is usually considered particularly important where the arylsulfonamide is to be used as a polymer-modifying additive, e.g., plasticizer in the preparation of thermosetting resins.

It has now been found that arylsulfonamides may be prepared without the multistep and costly purification of the aryl sulfonyl chloride intermediate and still function adequately in polymer modification of thermosetting resins and in forming sulfonamide-formaldehyde resins.

SUMMARY OF THE INVENTION

The invention is a process for the preparation of arylsulfonamides which comprises the steps of (a) reacting an aryl hydrocarbon with chlorosulfonic acid to form a crude chlorosulfonation reaction product containing an aryl sulfonyl chloride, (b) combining in an aqueous media said crude reaction product and a source of ammonia in reactive contact to form an amidation reaction mixture, (c) maintaining the temperature of the reaction mixture at between about 40° C. and 70° C. and the pH at above about 7 for a period of time sufficient to form an amidation reaction product containing an arylsulfonamide, and optionally (d) separating the resulting arylsulfonamide from the amidation reaction product.

In a particular aspect of the invention, toluenesulfonamides are prepared by the steps of: (a) reacting toluene with chlorosulfonic acid to form a crude chlorosulfonation reaction product containing toluene sulfonyl chloride, (b) combining in an aqueous media said crude reaction product and a source of ammonia to form an amidation reaction mixture, (c) maintaining the temperature of the reaction mixture at between about 40° C. and 70° C. and the pH at above about 7 for a period of time sufficient to form an amidation reaction product containing toluenesulfonamide and optionally (d) separating the resulting toluenesulfonamide from the amidation reaction product.

In another aspect of the invention, sodium hydroxide or another suitable basic material may be used to neutralize the acidic by-products formed in steps (a) and/or (c) above.

DESCRIPTION OF THE PREFERRED EMBODIMENTS

The process of the invention may be illustrated by the following reaction sequence wherein toluene is used as an example of the aromatic hydrocarbon.

$$CH_3C_6H_5 + ClSO_3H$$
$$\downarrow$$
$$CH_3C_6H_4SO_2Cl + (CH_3C_6H_4)_2SO_2 + ClSO_3H + H_2SO_4 + HCl + CH_3C_6H_4SO_3H$$
$$\downarrow NH_3, H_2O$$
$$CH_3C_6H_4SO_2NH_2 + (CH_3C_6H_4)_2SO_2 + (NH_4)_2SO_4 + NH_4Cl + CH_3C_6H_4SO_3NH_4$$

Organic Phase       Aqueous phase

This process improvement avoids the multistep operation used to separate and refine the aryl sulfonyl chloride in the crude reaction product which is typically carried out. In the process of the present invention, in one step, the aryl sulfonamide is formed directly from the crude reaction product and the acidic by-products in said crude reaction product may be neutralized.

The process of the invention begins with the reaction of an aryl hydrocarbon (including those with halogen substituents) with chlorosulfonic acid to form a crude chlorosulfonation reaction product containing an aryl sulfonyl chloride. The aryl hydrocarbon may be any aryl hydrocarbon ring compound which is suitable for reaction with the chlorosulfonic acid, for example, benzene, chlorobenzene, bromobenzene, fluorobenzene, iodobenzene, toluene, cumene, orthoxylene, ethyl benzene, n-propyl benzene, n-butyl benzene, n-hexyl benzene, n-octyl benzene, n-nonyl benzene, or other alkyl substituted benzene compounds, naphthalene and substituted naphthalenes and the like. Benzene and toluene are preferred with toluene being especially preferred. The chlorosulfonic acid should be substantially pure since more than trace amounts of impurities may cause undesirable side reactions.

The crude reaction product formed by the reaction of chlorosulfonic acid and the aryl hydrocarbon comprises a mixture of, for example, in the case of toluene as the aryl hydrocarbon, a major portion of toluene sulfonyl chloride isomers (principally ortho and para), and minor amounts of bis-tolylsulfone, unreacted chlorosulfonic acid, sulfuric acid, hydrochloric acid and toluene sulfonic acid. The specific composition and percentages of ingredients in the crude reaction product will, of course, vary with the type of aryl hydrocarbon employed in the reaction and the ratio of reactants used.

The crude chlorosulfonation reaction product containing the aryl sulfonyl chloride is next combined in an aqueous media with ammonia to form an amidation reaction mixture wherein, the arylsulfonamide is produced and the resulting acidic by-products are neutralized. The ammonia may be used in the form of an aqueous solution or may be introduced in the gaseous state into the aqueous media.

Neutralization of the acids formed during the course of the process may be effected by any suitable means compatible with the reaction. Generally, enough ammonia is used to neutralize all of the acids produced as well as to form the sulfonamide. But alkali or alkaline earth metal hydroxides may also be used to neutralize the acids. The alkali metal hydroxides include sodium hydroxide, potassium hydroxide and lithium hydroxide. Alkaline earth metal hydroxides such as magnesium hydroxide and calcium hydroxide may also be used. Sodium hydroxide is preferred.

The temperature of the amidation reaction mixture is maintained at between about 40° C. and 70° C., preferably, between about 45° C. and 65° C. by heating or cooling as needed or by rate of mixing. The heat of reaction will usually be sufficient to maintain the desired temperature with little or no additional heating being required. The pH of the amidation reaction mixture is maintained in a basic condition, i.e., above about 7 and, most preferably, between 8 and 11. In order to insure completion of the reaction, the temperature is maintained at reaction level after sulfonyl chloride addition is complete for a period of time of from about 30 minutes up to 2 hours or more, depending on the reactants involved.

In conducting the process of the invention, the proportions of reactants are based on the amount of aryl hydrocarbon used. Generally, from about 1.5 to about 4.0 moles, preferably 2 to 3 moles, of chlorosulfonic acid and from about 0.5 to about 0.9 moles, preferably 0.6 to 0.8 moles, of ammonia are used for each mole of aryl hydrocarbon. If ammonia is also used to neutralize the acidic by-products formed during the course of the process, about 4 to 6 additional moles are needed. Or sodium hydroxide, usually about 4.0 to 6.0 moles, may be used to neutralize all of the acid present and keep the pH at 7 or higher.

Isolation of the resulting arylsulfonamide product is convenient due to the fact that the amidation reaction product readily separates into two layers: an aqueous layer usually containing mostly by-products and an organic layer rich in the desired product. The organic layer may be a solid or a liquid, depending on the nature of the reactants. The organic layer containing the arylsulfonamide may be separated and used without further purification or it may be washed one or more times with water or with water made basic with ammonium hydroxide. The arylsulfonamide product may then be dried by warming, preferably at reduced pressure. Filtration of the product while it is in the molten state or recrystallization of solids are sometimes used to remove traces of impurities.

The arylsulfonamides produced by the process of this invention are usually mixtures of isomers, largely ortho- and para-substituted, and lesser amounts of meta isomers and residual sulfones. The process is particularly useful when such product mixtures can be used without further purification, e.g., in plasticizer applications and in sulfonamide-formaldehyde resins.

The invention is further illustrated by the following examples in which all parts and percents are by weight unless otherwise indicated.

EXAMPLE 1

Preparation of Crude and Refined Toluenesulfonyl Chloride

Chlorosulfonic acid and toluene (2.4 to 1 molar ratio) are fed in separate streams onto the surface of an agitated heel of crude toluenesulfonyl chloride mixture from a previously prepared chlorosulfonation batch held at 25°-30° C. in a 2000 gal. reactor. The crude chlorosulfonation reaction product is then fed into a quenching vessel along with chilled water and toluene. the quenched product overflows into a quencher separator where the aqueous acid comes to the top and overflows into an acid neutralizing vessel. The quenched organic layer is pumped to a two stage washing system to remove acid contamination and then into a jacketed glass-lined dehydrator where dehydration is carried out under 25 mm (3333 Pa) Hg vacuum and 80° C. pot temperature. The dehydrated product then goes into a detoluenation still where the remaining toluene is removed under 17-19 mm (2266-2533 Pa) Hg and pot temperature of 124°-126° C. The detoluenated product is then fed into a still where a purified mixture of toluenesulfonyl chloride isomers (about 65% para, 34% ortho, and 1% meta) is separated, leaving sulfones and other undesired residues for disposal.

EXAMPLE 2

Preparation of Toluenesulfonamide from Crude Unrefined Chlorosulfonation Reaction Product Using Ammonia to Neutralize Acids In a demonstration of the advantages of using the crude chlorosulfonation reaction product of the present invention instead of the purified toluenesulfonyl chlorides obtained by the complex, multistep quenching, washing, dehydration, detoluenation and distillation process described in Example 1, a 591.3 gms portion of the crude chlorosulfonation reaction product of Example 1 and 566.2 gms of ammonium hydroxide (28-30% NH$_3$) were added simultaneously to 750 ml of water over a period of 1 hour while stirring and cooling at 55°±2° C. to form an amidation reaction mixture. The pH was kept at 7.9 to 8.1 during the addition and while warming was continued for 1 hour more at 55°-60° C. The amidation reaction mixture was cooled to 20° C., filtered, and the solid was washed with water. It was then stirred in water at 50° C. and again cooled to 20° C. and washed with water. Drying in a vacuum oven at 55° C. gave 196.5 gms of product having a proton NMR spectrum that was consistent with the desired structure. GC analysis showed that the product was 98.2% toluenesulfonamides (para/ortho isomer ratio 2.4), the remaining 1.8% being largely sulfones. Except for the presence of sulfones, this product is essentially equivalent to toluenesulfonamide that is prepared from purified toluenesulfonyl chloride obtained by the multistep process of Example 1.

EXAMPLE 3

Preparation of Toluenesulfonamide from Crude Unrefined Chlorosulfonation Reaction Product Using Sodium Hydroxide to Neutralize Acids A 1160.4 gms portion of the crude chlorosulfonation reaction product of Example 1 was added to a stirred solution of 303 gms of ammonium hydroxide (28–30% ammonia), 100 g of 50% NaOH and 750 ml of water at 50°-55° C. until the pH reached 9, and then more 50% NaOH was added simultaneously, keeping the pH at 9.0-9.5, during the remainder of the chlorosulfonation addition. The amidation reaction mixture was warmed at 50°-55° C. with the pH at 9.0 for 0.5 hour, and then it was cooled to 20° C., filtered, and the solid was washed and dried as in Example 2, giving 313.3 gms of toluenesulfonamide mixture having a proton NMR and GC analysis essentially identical to the product obtained by the ammonia neutralization process of Example 2.

EXAMPLE 4

Preparation of Toluenesulfonamide, Using Ammonia to Neutralize Acids

Toluene (92.1 gms, 1.0 mole) was added to 291.3 gms (2.5 moles) of stirred chlorosulfonic acid cooled at 25°-30° C. over a period of 0.5 hour. Stirring was continued at 25° C. for 4 hours, and then the resulting crude chlorosulfonation reaction product was added subsurface to 382.6 gms of ammonium hydroxide (28–30% NH$_3$), diluted further with 1 liter of water, in 1.5 hours with cooling at 55°-65° C. Warming was continued at 60° C. with the pH maintained above 8 for 0.75 hour more. The amidation reaction mixture was then cooled to 25° C. and filtered. The solid isolated in this way was washed with water at 50° C. and dried in a vacuum oven at 80°/0.15 mm (20 Pa) Hg, giving 108.8 gms of solid having a proton NMR spectrum that was consistent with the toluenesulfonamide structure. This product is essentially identical to the toluene-sulfonamide products of Examples 2 and 3.

EXAMPLE 5

Preparation of N-Butylbenzenesulfonamide n-Butylbenzene (100 gms, 0.75 mole) was added to 305.8 gms (2.62 moles) of chlorosulfonic acid stirred and cooled at 12°-17° C. over a 2.4 hour period. After standing overnight, the resulting crude chlorosulfonation reaction product was added to a stirred solution of 395 gms of ammonium hydroxide and 100 gms of additional water with cooling at 45°-57° in 1.4 hours. After 1 hour more at 50°-55° C., 200 gms of toluene was stirred in, and then the toluene layer was separated, washed with water, decolorized by permanganate-sodium metabisulfite treatment, again water washed, and then dehydrated by warming to 120°/1 mm (133 Pa) Hg, giving 119.7 gms (75% yield) of light yellow liquid having a proton NMR spectrum consistent with the N-butylbenzenesulfonamide structure.

EXAMPLE 6

Preparation of Chlorobenzenesulfonamide

Chlorobenzene (112.6 gms, 1.0 mole) was added to 291.3 gms (2.5 moles) of stirred chlorosulfonic acid cooled at 25°-30° C. over a period of 1.5 hours. After 1.5 hours at 30°-40° C. the crude chlorosulfonation reaction product was added subsurface to a stirred solution of 400 gms of ammonium hydroxide (28–30% ammonia) and 500 ml of additional water cooled at 50°-55° C. over a period of 1.5 hours. The amidation reaction product was warmed at 50°-60° C. for 0.5 hour, and then it was cooled to 20° C. and filtered, giving a white solid which was washed with dilute ammonium hydroxide at 50°-60° C. and then with deionized water at 10°-15° C. Drying of the product in a vacuum oven at 70° C. gave 133 gms, m.p. 129°-144° C., having a proton NMR spectrum consistent with the chlorobenzenesulfonamide structure.

Although this invention has been described with respect to specific embodiments, the details thereof are not to be construed as limitations, for it will be apparent that various equivalents, changes and modifications may be resorted to without departing from the spirit and scope thereof and it is understood that such equivalent embodiments are intended to be included herein.

We claim:

1. A process for the preparation of arylsulfonamides comprising the steps of: (a) reacting an aryl hydrocarbon with chlorosulfonic acid to form a crude chlorosulfonation reaction product, (b) combining in an aqueous media said crude chlorosulfonation reaction product and a source of ammonia in reactive contact to form an amidation reaction mixture, (c) maintaining the temperature of the amidation reaction at between about 40° C. and 70° C. and the pH at above about 7, for a period of time sufficient to form an amidation reaction product comprising an organic phase and an aqueous phase, said organic phase being rich in arylsulfonamide, and said aqueous phase containing mostly by-products of said amidation reaction product, and (d) separating said organic phase from said aqueous phase.

2. The process of claim 1 wherein the aryl hydrocarbon is an alkyl benzene compound wherein the alkyl group contains from 1 to 15 carbon atoms.

3. The process of claim 2 wherein the alkyl group is selected from methyl, ethyl, n-butyl, isopropyl, octyl and cyclohexyl.

4. The process of claim 1 wherein the temperature is 45° C. to 65° C.

5. The process of claim 1 wherein the pH is from about 8 to about 11.

6. The process of claim 1 wherein from about 1.5 to 4.0 moles of chlorosulfonic acid and about 5 to 7 moles of ammonia are used for each mole of aryl hydrocarbon.

7. The process of claim 1 wherein from about 1.5 to 4.0 moles of chlorosulfonic acid, about 0.5 to 0.9 moles of ammonia, and additionally about 4.0 to 6.0 moles of alkali metal hydroxide are used for each mole of aryl hydrocarbon.

8. The process of claim 1 wherein the aryl hydrocarbon is halogen-substituted.

9. A process for the preparation of toluenesulfonamide comprising the steps of: (a) reacting toluene with chlorosulfonic acid to form a crude chlorosulfonation reaction product containing toluene sulfonyl chloride, (b) combining in an aqueous media said crude reaction product and a source of ammonia in reactive contact to form an amidation reaction mixture, (c) maintaining the temperature of the amidation reaction mixture at between about 40° C. and 70° C. and the pH at above 7 for a period of time of from 30 minutes up to about 2 hours to form an amidation reaction product comprising an organic phase and an aqueous phase, said organic phase being rich in toluenesulfonamide and said aqueous phase containing mostly by-products of said amidation reaction product, and (d) separating said organic phase from said aqueous phase.

10. The process of claim 9 wherein the temperature is from about 45° C. to 65° C.

11. The process of claim 9 wherein the pH is from about 8 to 11.

12. The process of claim 9 wherein the toluenesulfonamide product comprises from 40 to 80 percent para orientation.

13. The process of claim 9 wherein the product contains from 1 to 3 percent of tolylsulfones.

14. The process of claim 8 wherein the halogen is chlorine.

15. The process of claim 8 wherein the halogen is bromine.

16. The process of claim 8 wherein the halogen is fluorine.

* * * * *